United States Patent [19]

Yeaney et al.

[11] Patent Number: 4,593,822
[45] Date of Patent: Jun. 10, 1986

[54] WIRE RACK WITH REMOVABLE REPLACEABLE SLEEVES

[75] Inventors: Gerald L. Yeaney; Roy S. Klein, both of Erie, Pa.

[73] Assignee: American Sterilizer Company, Erie, Pa.

[21] Appl. No.: 629,230

[22] Filed: Jul. 9, 1984

[51] Int. Cl.⁴ .............................................. A47G 19/08
[52] U.S. Cl. ........................................ 211/41; 211/181
[58] Field of Search ................... 211/40, 41, 42, 43, 211/181, 184; 118/500

[56] References Cited

U.S. PATENT DOCUMENTS

| 428,555 | 5/1890 | Dom | 211/181 X |
| 1,268,946 | 6/1918 | Farris | 248/448 |
| 2,804,213 | 8/1957 | Fox | 211/41 |
| 3,096,008 | 7/1963 | Schumacher | 211/181 X |
| 3,693,808 | 9/1972 | Rauch | 211/181 |

FOREIGN PATENT DOCUMENTS 93962  5/1969  France .................. 211/41 R

*Primary Examiner*—J. Franklin Foss
*Assistant Examiner*—Sarah A. Lechok Eley
*Attorney, Agent, or Firm*—Robert D. Yeager; Christine R. Ethridge

[57] ABSTRACT

A rack for holding items in a washing, washing-sterilizing or sterilizing apparatus having a frame and a plurality of wire components, each wire component having at least one end releasably secured to the frame. A plurality of sleeves, preferably made of a silicon based elastomer, are provided. One sleeve encloses the length of each wire component and is sufficiently flexible to substantially conform to the configuration of the component on which the sleeve is disposed. The sleeves are removable for selective replacement thereof.

5 Claims, 3 Drawing Figures

WIRE RACK WITH REMOVABLE REPLACEABLE SLEEVES

BACKGROUND OF THE INVENTION

1. Field of the Invention

The present invention relates to wire racks for use in washing and/or sterilizing apparatus, and more particularly to wire racks having wire components with at least one releasably secured end for receiving a removable, replaceable sleeve.

2. Description of the Prior Art

The wire racks used to hold items in washing apparatus are generally coated to prevent mechanical abuse, such as denting and abrasion, to the items from direct contact with the wire components of the racks. The coating, generally nylon, cannot withstand prolonged repeated exposures to the high temperatures of the steam in washer sterilizers. The temperatures in washer-sterilizers and sterilizers for use in the health care field rise to about 250° F. or greater. The coating on the racks used in such apparatus eventually breaks down and falls away from the wire components, exposing the items in the rack to mechanical abuse. Additional deterioration of the coating may occur from sharp edges on the items held in the rack.

Unless the wire components are made of a noncorrosive material, repeated exposure of the bare wire component to the moisture in the apparatus can result in corrosion of the rack, thus shortening the useful life of the rack. Where noncorrosive materials are used in the rack, the deterioration of the coating and the consequential mechanical abuse of the items held in the rack can shorten the useful lives of both the items and the rack.

Accordingly, there is a need for a rack for use in an apparatus for washing-sterilizing or sterilizing which has a prolonged useful life and which protects the items it holds from mechanical abuse. There is a further need for such a rack having a coating which will not contribute to the deterioration of the rack or the items it holds.

SUMMARY OF THE INVENTION

The present invention provides a device for holding items in an apparatus for washing, washing-sterilizing or sterilizing which has a prolonged useful life and which protects the items it holds from mechanical abuse by providing a removable sleeve which cushions the items and which can be replaced when worn.

The device includes a rack having a frame and a plurality of wire components arranged to support the items, each of the components having at least one end releasably secured to the frame, and a plurality of sleeves. One of the sleeves is so slidably disposed on each of the components that each sleeve so encloses the one component on which the sleeve is disposed that the plurality of sleeves can cushion the items against mechanical abuse from the components. Each sleeve is continuous for the length of the component on which the sleeve is disposed and each sleeve is sufficiently flexible to substantially conform to the configuration of the component on which the sleeve is disposed. Each sleeve is removable from the component on which the sleeve is disposed for selective replacement thereof.

In the preferred embodiment, each component has a first end releasably secured to the frame and a second end fixedly secured to the frame. The sleeves are preferably made of an elastomeric material which may be a material suitable for use in a steam environment of about 250° F., such as a silicon based elastomer.

BRIEF DESCRIPTION OF THE DRAWINGS

The following detailed description of the preferred embodiment can be better understood if reference is made to the attached drawings in which.

DETAILED DESCRIPTION OF THE PREFERRED EMBODIMENT

Figure 1:
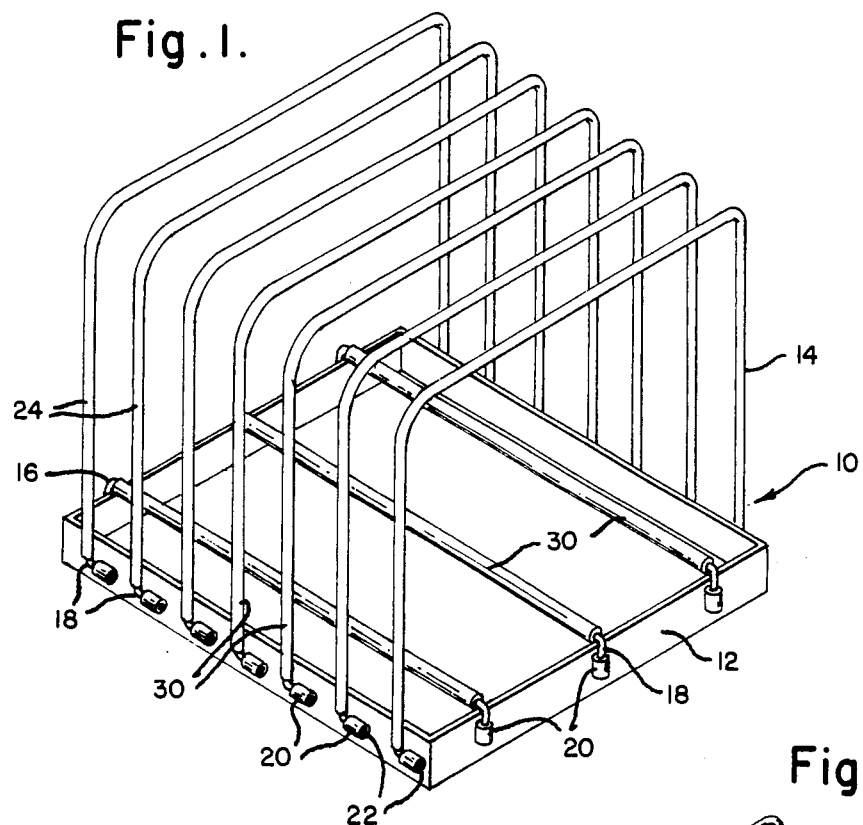
FIG. 1 is a perspective view of a rack having the features of the preferred embodiment of the present invention.
Figure 2:
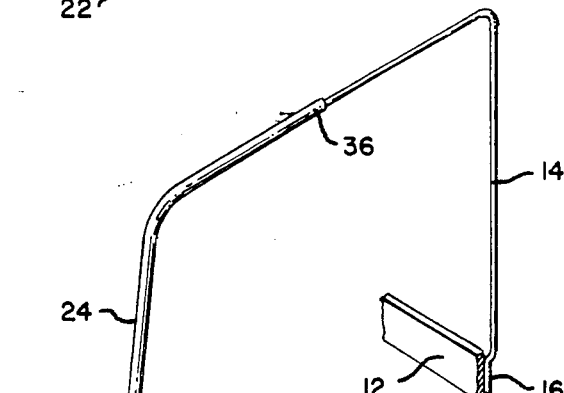
FIG. 2 is a sectional view of the rack of FIG. 1.
Figure 3:
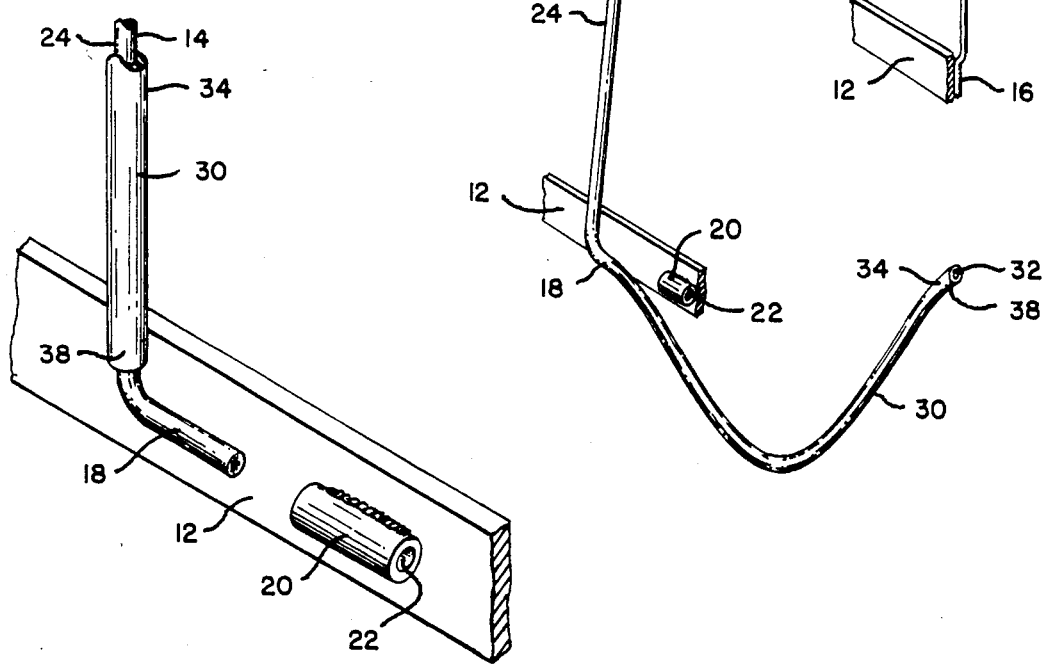
FIG. 3 is a sectional view of the rack of FIG. 1.

FIGS. 1 through 3 illustrate the preferred embodiment of rack 10 of the present invention.

Rack 10 includes frame 12 and wire components 14. Each wire component 14 has one end 16 fixed by any suitable known means, such as welding, to the frame 12.

The other end 18 of each wire component 14 is free and may be releasably secured to frame 12 by any suitable known means. A boss 20 having a recess 22 is shown in FIG. 1 as the preferred means of securing end 18 to frame 12. End 18 can slide into and out of recess 22 by applying a sufficient amount of pressure to the vertical leg 24 of the wire component 14 to move end 18. The wire component 14 is preferably made of a rigid yet resilient material so that repeated applications of pressure to leg 24 will not bend or snap the wire component 14.

The wire components 14 may be arranged in any suitable known manner to support items in the rack, provided at least one end of each wire component 14 can be removably attached for accommodating the removable sleeve. One possible arrangement is shown in U.S. Ser. No. 629,168, filed 7/9/84, for WIRE RACK FOR PROCESSING RIGID CONTAINERS IN WASHING AND/OR STERILIZING APPARATUS filed on the same date herewith, which is incorporated herein by reference.

Sleeves 30 are shown in FIG. 3 as they appear while being applied to wire components 14. FIG. 1 shows the sleeves 30 as they are mounted on each of the wire components 14. Each sleeve 30 includes lumen 32, exterior surface 34, end 36 and end 38.

Sleeves 30 are preferably made of a heat resistant elastomeric material, such as a commercially available silicon based elastomer. The silicon based elastomer is particularly well suited for the high temperatures of steam sterilizers and washer-sterilizers which can be in excess of 250° F. While silicon based elastomers are preferred, any heat resistant material having sufficient flexibility and resilience to slide over the wire component 14 and conform to the configuration of the wire component 14 and which is also resistant to the chemical environment of the particular washer or sterilizer, will suffice.

Each sleeve 30 is cut to assume the length of the particular wire component 14 on which the sleeve 30 will be disposed. The diameters of lumens 32 of each sleeve 30 may be somewhat less than the diameters of the wire components 14 because of the flexible nature of the sleeves. The degree of flexibility of the chosen material determines how much less the lumen 32 diameter may be. The resiliency of the material allows it to be stretched over the wire components 14 and to conform to the configuration of each component 14.

The wire components 14 and the frame 12 of rack 10 are made of nickel (and it's alloys) or passivated stainless steel, which renders the rack 10 resistant to steam and aqueous corrosion. The stainless steel grade has three requirements: (1) that most corrosion resistant family, the austenitic family be used,; (2) that a low carbon austenitic grade be used to prevent intergranular corrosion, a condition caused by welding or brazing high carbon austenitic grades during fabrication; and (3) that the stainless be cleaned and passivated before the elastomeric sleeves are applied. Passivating insures that an oxide film, which is the source of the stainless steel's corrosion resistance, exists. This is necessary because the sleeve impedes the contact of the stainless with atmospheric oxygen, which would be the source for oxide film formation. In conventional coated racks, passivation is often eliminated because the metal components are not expected to be exposed to moisture. However, when the coating chips or deteriorates, such exposure occurs and corrosion follows.

Following passivation of the stainless steel rack, sleeves 30 can be slid onto wire components 14. The free end 18 of each wire component 14 is removed from recess 22 of boss 20 by applying sufficient pressure to leg 24 to pull end 18 out of recess 22. One end, 36 or 38, of sleeve 30, which has been cut to the desired length, is slid over free end 18 and pulled by the end, 36 or 38, over the wire component 14 to completely enclose the component in the sleeve 30. The free end 18 is reinserted into recess 22 of boss 20. Each wire component 14 is similarly enclosed by one sleeve 30.

The exterior surfaces 34 of sleeves 30 provide a cushion for the items held by rack 10 against mechanical abuse from the wire components 14. When a particular sleeve 30 begins to deteriorate or if it is torn, the sleeve 30 can be removed from the wire component 14 on which it is disposed. A new sleeve 30 can then replace the worn one. Because each wire component 14 has at least one free end 18, sleeves 30 can be individually replaced as it becomes necessary. In this way, the useful life of the rack 10 can be prolonged because the deterioration of one or more portions of any of the sleeves 30 does not necessitate discarding the entire rack. The useful life of the items held by the racks 10 can be prolonged because they do not have to be exposed to the bare wire components beneath worn or torn sleeves 30.

Although the wire components 14 of the preferred embodiments of rack 10 have one fixed end 16 and one free end 18, it should be appreciated that both ends may be releasably secured to frame 12, provided the means of securing the ends prevents rotation of the wire component 14 with respect to the frame 12.

What is claimed is:

1. A device for holding items in apparatus for washing, washing-sterilizing or sterilizing comprising:

a rack having a frame and a plurality of wire components arranged to support the items, each of said components having at least one end releasably secured to said frame; and a plurality of heat and moisture resistant sleeves, one of said sleeves being so slidably disposed on each of said wire components that each of said sleeves so encloses the one of said wire components on which said sleeve is disposed that said plurality of sleeves can cushion the items in said rack against mechanical abuse from said wire components, each of said sleeves being continuous for the length of the one of said wire components on which said sleeve is disposed and being sufficiently flexible to substanially conform to the configuration of the one of said wire components on which said sleeve is disposed, and each of said sleeves being removable from the one of said wire components for selective replacement thereof by releasing said releasably secured end and sliding said sleeve over said released end.

2. A device for holding items in apparatus for washing, washing-sterilizing or sterilizing comprising:

a rack having a frame and a plurality of wire components arranged to support the items, each of said components having a first end releasably secured to said frame and a second end fixedly secured to said frame; and a plurality of heat and moisture resistant sleeves, one of said sleeves being so slidably disposed on each of said wire components that each of said sleeves so encloses the one of said wire components on which said sleeve is disposed that said plurality of sleeves can cushion the items in said rack against mechanical abuse from said wire components, each of said sleeves being continuous for the length of the one of said wire components on which said sleeve is disposed and being sufficiently flexible to substanially conform to the configuration of the one of said wire components on which said sleeve is disposed, and each of said sleeves being removable from the one of said wire components for selective replacement thereof by releasing said releasably secured end and sliding said sleeve over said released end.

3. A device as recited in claim 2 wherein said sleeves are made of an elastomeric material.

4. A device as recited in claim 3 wherein said material is suitable for use in a steam environment of about 250° F.

5. A device as recited in claim 3 wherein said material is a silicon based elastomer.

* * * * *

UNITED STATES PATENT AND TRADEMARK OFFICE
CERTIFICATE OF CORRECTION

PATENT NO. : 4,593,822

DATED : June 10, 1986

INVENTOR(S) : Gerald L. Yeaney and Roy S. Klein

It is certified that error appears in the above—identified patent and that said Letters Patent is hereby corrected as shown below:

Col. 4, line 27, delete "the"; and

Col. 4, line 27, after "each of said" insert --wire--.

Signed and Sealed this

Ninth Day of December, 1986

Attest:

DONALD J. QUIGG

Attesting Officer

Commissioner of Patents and Trademarks